United States Patent [19]

Heiss

[11] Patent Number: 5,187,869
[45] Date of Patent: Feb. 23, 1993

[54] NIPPER INSTRUMENT FOR CUTTING SURGICAL NAILS, WIRES OR THE LIKE

[76] Inventor: Jürgen K. Heiss, Wilhelm-Hauff-Weg 5, 7200 Tuttlingen, Fed. Rep. of Germany

[21] Appl. No.: 691,548

[22] Filed: Apr. 25, 1991

[30] Foreign Application Priority Data

Apr. 27, 1990 [DE] Fed. Rep. of Germany ... 9004793[U]

[51] Int. Cl.⁵ .......................................... B26B 17/02
[52] U.S. Cl. ...................................... 30/189; 30/187; 30/191
[58] Field of Search ................. 30/249, 341, 175, 183, 30/186, 189, 193, 178, 179, 184, 191, 225, 187; 81/9.44

[56] References Cited

U.S. PATENT DOCUMENTS

| | | | |
|---|---|---|---|
| 1,435,131 | 11/1922 | Jacobson | 30/189 |
| 2,602,993 | 7/1952 | Armstrong | 30/249 |
| 2,647,312 | 8/1953 | Neal | 30/189 |
| 2,745,177 | 5/1956 | Kortick | 30/186 |
| 3,182,485 | 5/1965 | Sund | 30/191 |
| 3,772,783 | 11/1973 | Averitt | 30/186 |
| 3,902,206 | 9/1975 | Naquin | 30/90.6 |
| 4,058,893 | 11/1977 | Boyajian | 30/189 |
| 4,141,141 | 2/1979 | ViPond | 30/186 |

FOREIGN PATENT DOCUMENTS

| | | | |
|---|---|---|---|
| 277641 | 12/1969 | Austria | 30/189 |
| 253352 | 11/1948 | Switzerland | 30/249 |

Primary Examiner—Frank T. Yost
Assistant Examiner—Hwei-Siu Payer
Attorney, Agent, or Firm—Bachman & LaPointe

[57] ABSTRACT

A nipper instrument (10), in particular for cutting surgical nails, wires or the like, having a cutting mouth (14) which is defined by two cutting members (15, 15$_a$) at the head end of the nipper instrument, which at the other end has two handle ends (44, 45) of pivotally interconnected nipper arms (18, 40), which handle ends can be moved together into a cutting position of the cutting members against a return force, is provided with a cutting members (15$_a$) on a pivotal jaw (22) which is pivotably connected to a nipper arm (18) carrying the other cutting members (15) and bears with its free end (24) against a cam portion (42$_a$) of the other nipper arm (40), the curvature of which increases towards the cutting mouth (14). The free end (24) of the pivotal jaw (22) carries a shaft (26) for a roller (28) which bears against the cam portion (42$_a$), wherein an abutment surface (39) may be provided at the end of the cam portion (42$_a$) as a travel limiting device for the free end (24) of the cutting jaw (22) or for the roller (28).

13 Claims, 6 Drawing Sheets

NIPPER INSTRUMENT FOR CUTTING SURGICAL NAILS, WIRES OR THE LIKE

DESCRIPTION

The invention relates to a nipper instrument, in particular a nipper instrument for cutting surgical nails, wires or the like, having a cutting mouth which is defined by two cutting edges at the head end of the nipper instrument.

Nipper or pincer instruments or tools of that kind are required in particular in orthopaedics for cutting wires, nails or screw elements to length. In that situation, the prevention of chips or splinters or like particles of material in the cutting operation, in order to avoid infection, is a necessity from the hygiene point of view.

Having regard to that art, the inventor set himself the aim of so designing a nipper instrument of the kind set forth in the opening part of this specification that the user can effect an operation of severing elongate or shaped portions of material, as far as possible without the formation of chips or splinters, without applying a large amount of force, with one hand; the invention further seeks to provide that the force applied by the operator can be applied independently of the nature of the material and the size of the elongate portion, and as far as possible linearly.

That object is achieved by the teachings set forth in the respective independent claims. The appendant claims set forth improved configurations in relation thereto.

According to the invention, there is provided a cutting means on a pivotal jaw which is pivotally connected to a nipper arm carrying the other cutting means—for example a blade insert—and bears with its free end against a cam portion of the other nipper arm, the curvature of which increases towards the cutting mouth. In addition, in an advantageous fashion, the free end of the pivotal jaw is to carry on a shaft a roller which bears against said cam portion.

By virtue of the eccentric configuration in accordance with the invention, it is now possible for the force occurring at the cutting means to be rendered uniform by virtue of the curvature of the cam portion; for that purpose it has also proven to be advantageous for the cam portion, as a sliding guide for the roller on the nipper instrument, to be adapted to be interchangeable so that a nipper instrument can be used for different materials or areas of use.

The cam portion is advantageously part of a guide portion of the second arm of the nipper instrument and the path of movement of the guide portion is disposed at a spacing relative to the connection between the arms of the nipper instrument. It has also been found advantageous for the guide portion to be in the form of part of a head portion, which is triangular in side view, of the second arm of the nipper instrument, wherein one side of the triangle, which extends the handle end of the arm of the nipper instrument, has the cam portion and the other two sides of the triangle extend from the end of the cam portion and from the handle end respectively, and meet at the connection between the arms of the nipper instrument.

A consideration of particular significance in accordance with the invention is the association of the connections or axes: a straight line connecting the connection between the pivotal jaw and the arm of the nipper instrument with the roller axis should preferably define, with a straight line which passes through that roller axis and the connection of the arms of the nipper instrument, an angle which is a little larger than 90° and which in particular is between 96° and 104°.

In order to restrict the eccentric movement, it has been found advantageous to have an abutment surface which is provided by an abutment projection which extends approximately on a line perpendicular to the guide portion through the connection between the arms of the nipper instrument.

In accordance with a further feature of the invention the spacing of the connection between the one arm of the nipper instrument and the pivotal jaw, and the end of the nipper instrument, is shorter than the spacing of said connection from the roller at the end of the pivotal jaw.

An aspect of independently inventive significance involves a nipper instrument in which—possibly in combination with the above-indicated features—the cutting mouth has at least two zones with a different cutting spacing, wherein at least one of the cutting edges is divided by a step surface extending transversely to the axis of the nipper instrument into cutting portions of which that which is more remote from the free end of the cutting mouth preferably bears in the closed condition of the nipper instrument against the oppositely disposed cutting edge. By virtue of that feature, a pair of cutting edges, in the cutting operation, do not now have to pass through the entire cross-section of the wire; the pair of cutting members with the widest spacing between their cutting edges, which are advantageously provided at the free end of the cutting mouth, notch the wire which is then pushed to the next cutting stage; the cutting edges thereof are associated more closely with each other and can penetrate further into the material, with the application of a small amount of force.

The number of cutting stages is dependent on the nature of the material or wire or the like to be severed, while their spacings from each other, which are normal to the longitudinal axis of the nipper instrument, are preferably equal or increase somewhat towards the deepest point of the cutting mouth of the instrument. In accordance with another feature of the invention the cutting edges of the one or other pair of cutting members, when in the closed position of the cutting mouth, may even extend at an angle to the longitudinal axis of the cutting mouth in order to produce completely parallel cut grooves in that cutting stage.

With two cutting portions and with two mutually aligned step surfaces, the height thereof respectively corresponds approximately to a quarter of the length of a severing cut or the diameter of a wire.

It has also been found advantageous for the axial length of the cutting portions to be approximately equal.

It is also in accordance with the invention for each cutting jaw to have at least one run-on or check surface which, when the cutting mouth is in a closed condition, bears against a run-on or check surface of the other cutting jaw; that arrangement effectively prevents the cutting edges from over-running each other.

The run-on or check surface of the cutting jaw is preferably aligned with the cutting edge thereof. It has also been found advantageous for the cutting edge to extend between two run-on or check surfaces of the cutting jaw or for the run-on or check surfaces of the cutting jaw to be provided on two horn portions and for the latter to be connected by a cutting edge; that configuration enhances the stability of the cutting member or cutting edge.

Further advantages, features and details of the invention will be apparent from the following description of preferred embodiments and with reference to the drawings showing diagrammatic views in which:

FIG. 3 is a perspective view of another nipper or pincer instrument in a rest position, FIG. 4 shows the nipper instrument of FIG. 3 in a cutting position, FIGS. 5 and 7 each show a further perspective view of a nipper or pincer instrument in a cutting position, FIG. 8 is a view on an enlarged scale of the nipper instrument head of FIG. 7 with two cutting jaws.

Figure 1:
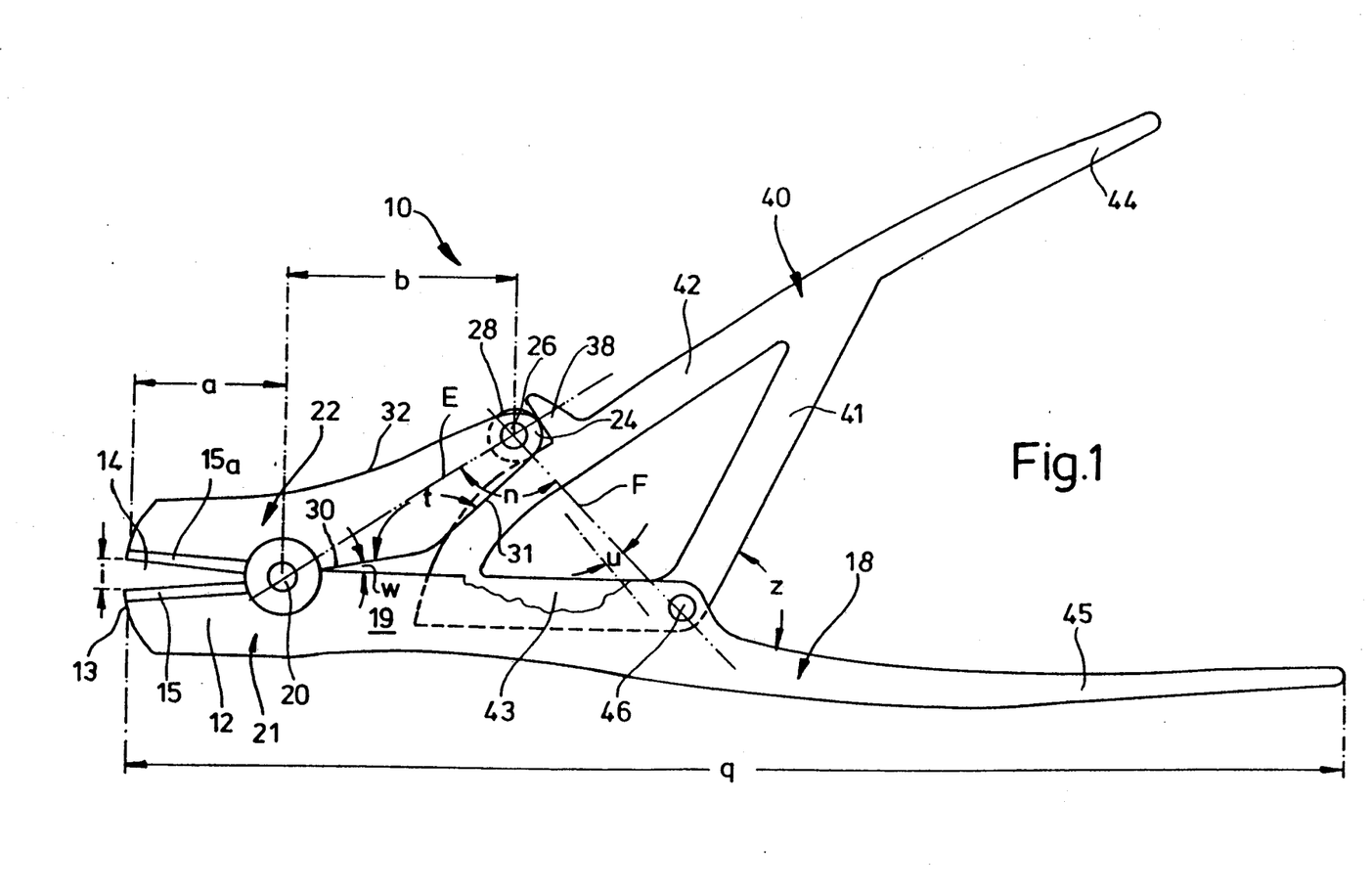
FIG. 1 is a side view of a nipper or pincer instrument for surgical uses in a rest position.
Figures 2, 6:
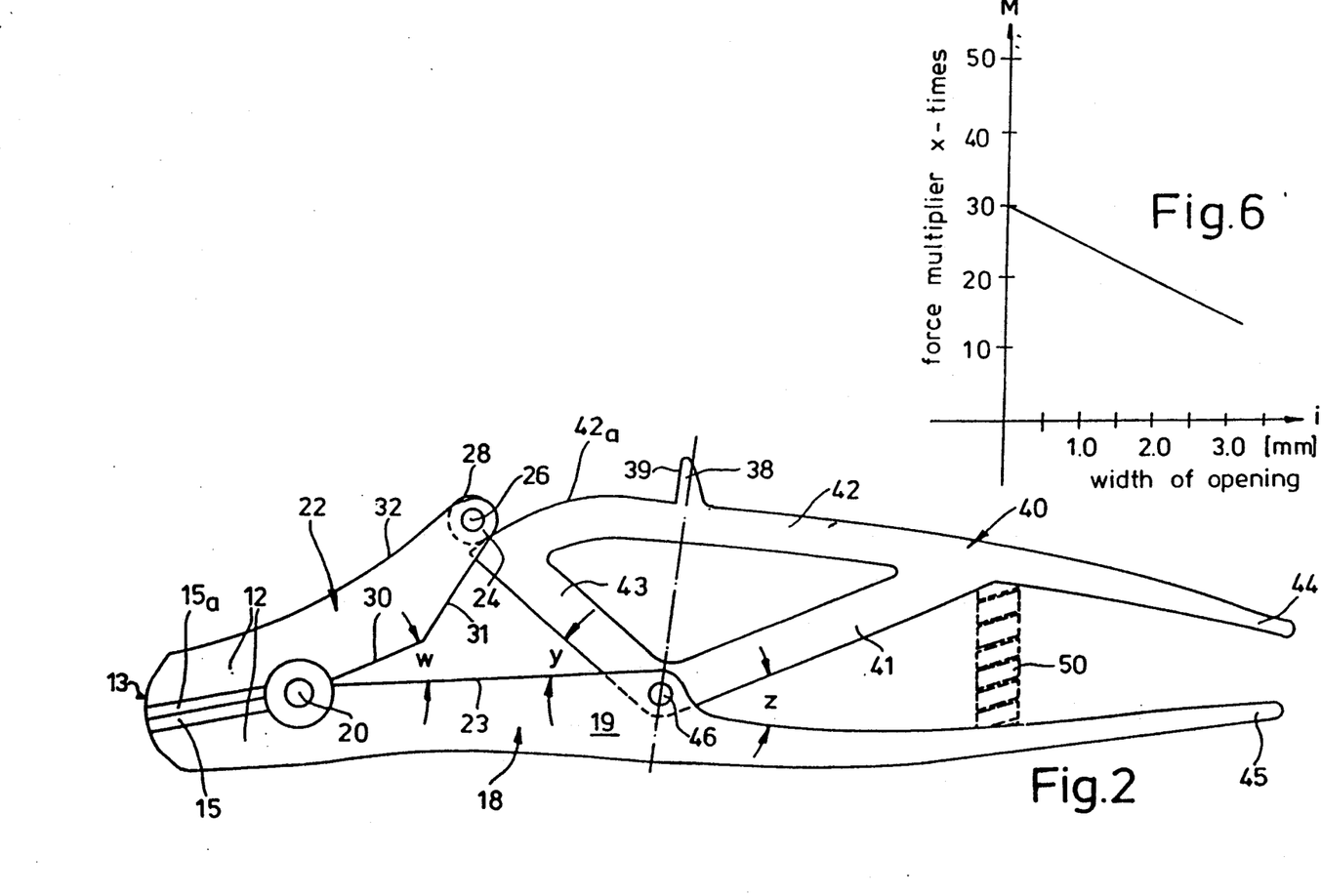
FIG. 2 shows the nipper instrument of FIG. 1 in a cutting position.
FIG. 6 is a graph relating to a cutting operation.

A nipper or pincer instrument 10 for cutting surgical nails, wires or the like substantially without chips or splinters, by means of two mutually oppositely disposed cutting inserts 15, 15$_a$ which define a cutting mouth 14 in a nipper instrument head 12 comprises a one-piece nipper arm 18 which can be seen at the bottom of FIGS. 1 and 2 and which determines the length q of the nipper instrument 10 and which at one end is in the form of a conically tapering pressing leg 21 in which the cutting insert 15 fits. The cutting inserts 15, 15$_a$ are not shown in FIGS. 3 through 5 for the sake of clarity of the drawing.

Pivotally connected to the nipper arm 18 at the end of the one cutting insert 15 which it provides, by means of a head connection 20, is a pivotal jaw 22 which is provided with the other cutting insert 15$_a$. The pivotal jaw 22 is kidney-shaped in side view and carries a roller 28 at its free end 24 which is remote from the cutting insert 15$_a$, at a pin-like axis as indicated at 26. The spacing a of the head joint 20 from the end 13 of the nipper instrument is shorter than its spacing b relative to the pin 26 carrying the roller 28.

In the rest position shown in FIG. 1, the pivotal jaw 22 defines an acute angle w with the nipper arm 18 which is here formed by two side plates 19 of a U-shaped profile portion, behind the head joint 20, as viewed from the cutting mouth 14 which is open with a spacing i between the cutting inserts 15 and 15$_a$. The jaw contour 30 which defines that angle w is followed at an obtuse angle t by a jaw edge 31 which, with a slightly inwardly curved outside edge 32 of the pivotal jaw 22, defines the free end 24 of the jaw.

Figures 3, 4, 5:
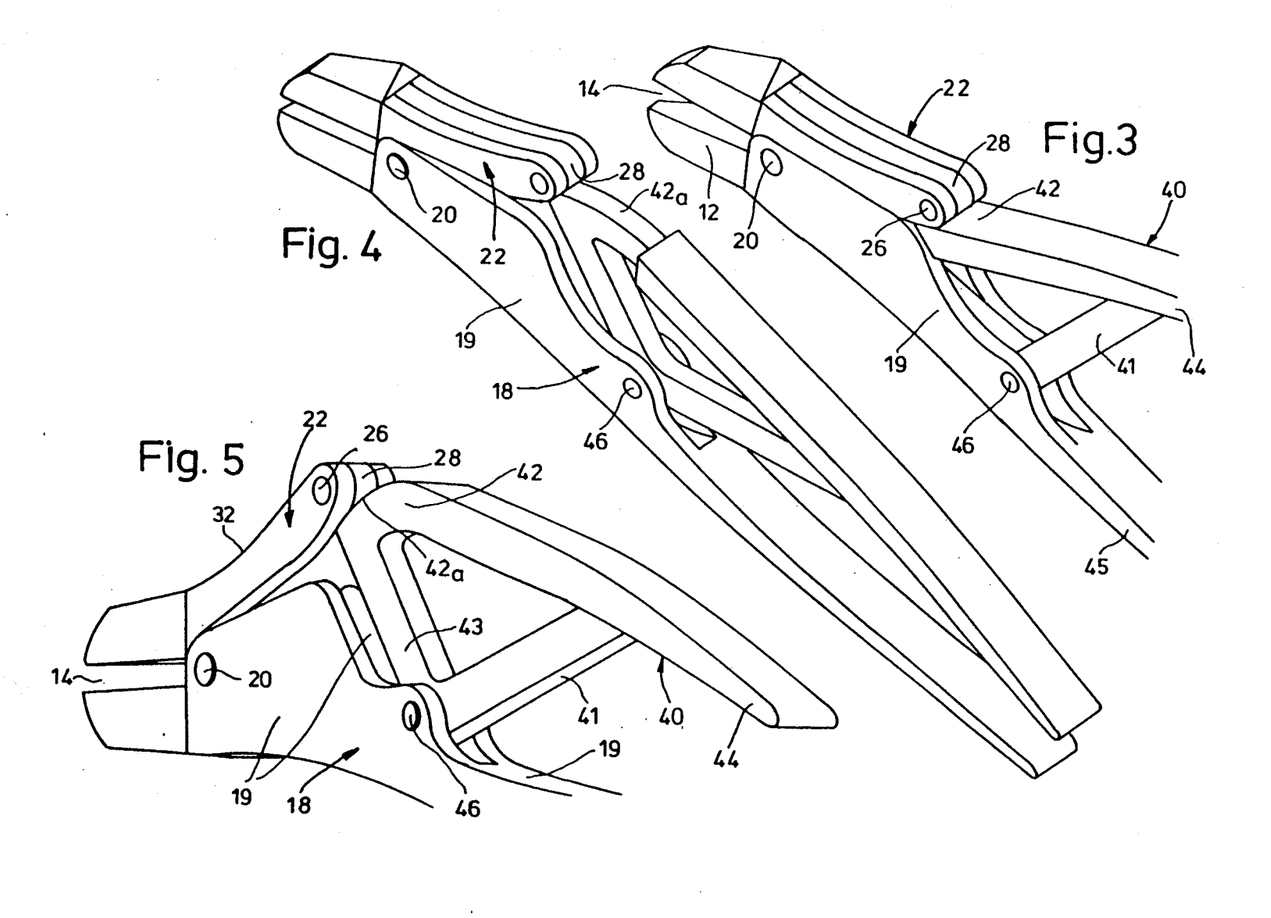

As shown in FIG. 1, the roller 28 bears against an abutment projection 38, which is not to be found in the embodiments illustrated in FIGS. 3 through 5, of a pressure arm 40 which is pivotably associated with the nipper arm 18 and which towards the roller has a guide portion 42 and adjoining same a handle end 44 which projects rearwardly therefrom. The handle end 44, with a handle end 45 of the nipper arm 18, represents the nipper instrument handle, the cooperating components 44 and 45 of which are moved towards each other during a severing operation, that is to say when moving from the rest position shown in FIG. 1 into the severing position shown in FIG. 2, with the nipper or closing angle z becoming progressively smaller.

The guide portion 42 of the arm 40, when viewed as a side view, forms an integral triangle with an inclined limb portion 41 and an end limb portion 43. The inclined limb portion 41 and the end limb portion 43 meet at a mounting location through which passes a hinge pin 46; the hinge pin 46 connects the arm 40 to the nipper arm 18 in such a way that the latter delimits the nipper angle z, with the inclined limb portion 41.

FIG. 1 shows that a straight line E connecting the head connection 20 and the axis 26 of the roller 28 forms with a connecting straight line F an angle n which is larger than 90° by an acute supplemental angle u of about 10°.

The abutment projection 38 provides the roller 28 with an abutment edge 39 from which the guide portion 42 extends straight over a short distance and is then curved about the hinge pin 46 in the manner of a cam portion 42$_a$ as a sliding guide for the roller 28.

If the nipper angle z is reduced against the force of a spreading spring which is only diagrammatically indicated at 50, then on the one hand an angle y is increasingly opened between the end limb portion 43 of the arm 40 and a straight inside edge 23 of the nipper arm 18. On the other hand, the roller 28 moves down the cam portion 42$_a$, the curvature of which increases with increasing spacing from the abutment surface 39 and thus uniformly increases the force acting on the cutting inserts 15, 15$_a$, as can be seen from FIG. 6 in regard to the configuration of a straight line G in relation to the width of opening i of the cutting mouth 14; plotted vertically thereto in FIG. 6 is the x-times force multiplier M.

FIGS. 3 and 4 particularly clearly show that the triangle 41, 42, 43 is mounted in such a way as to be guided between the side plates 19 of the nipper arm 18 and moves downwardly towards the rest position into the U-shaped configuration (see FIG. 3).

The cutting inserts 15 and 15$_a$ are thus moved by an eccentric system which permits the above-mentioned effect of rendering the force uniform.

Figures 7, 8:
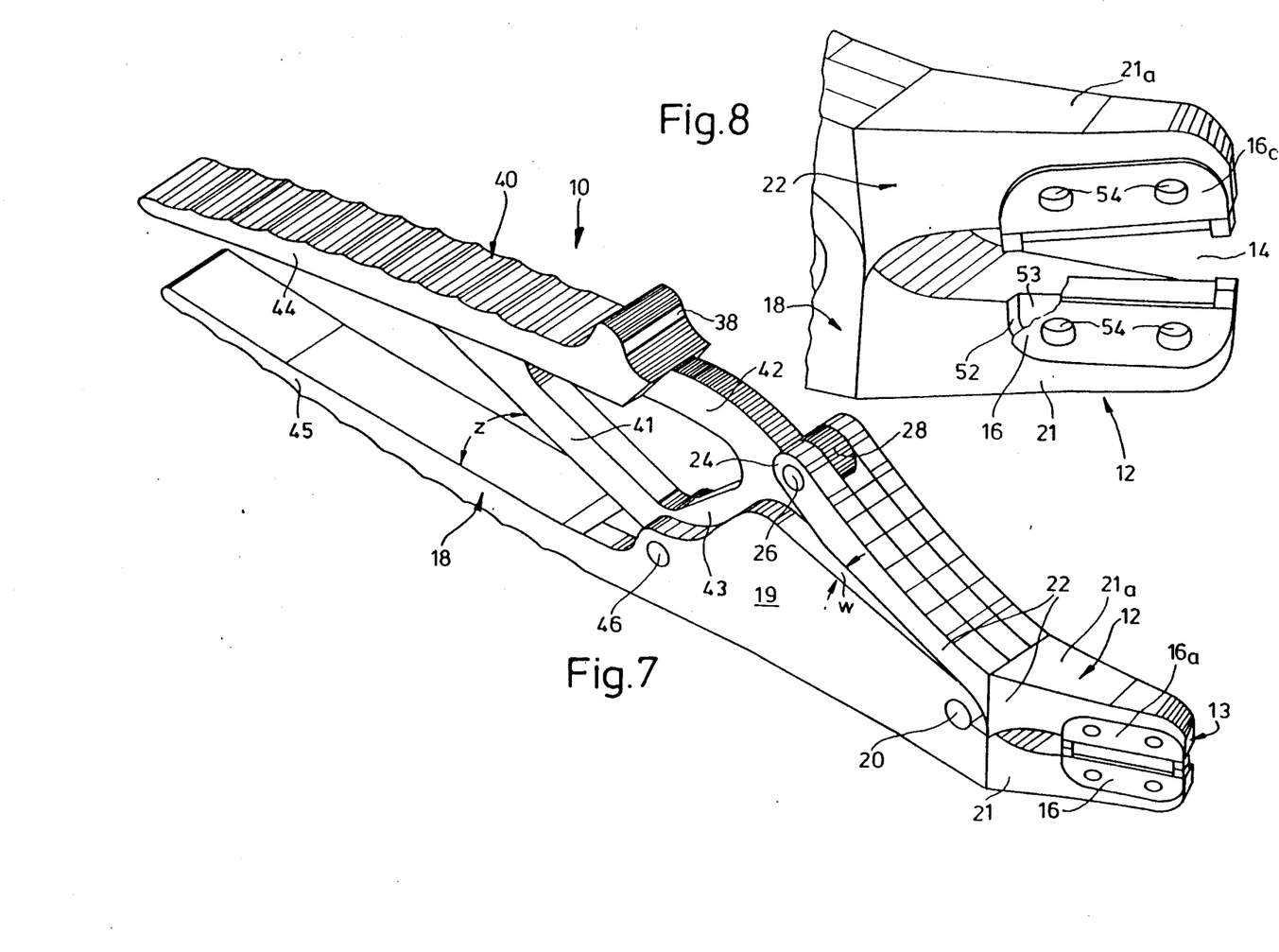
Figures 9, 10, 11, 12, 13:
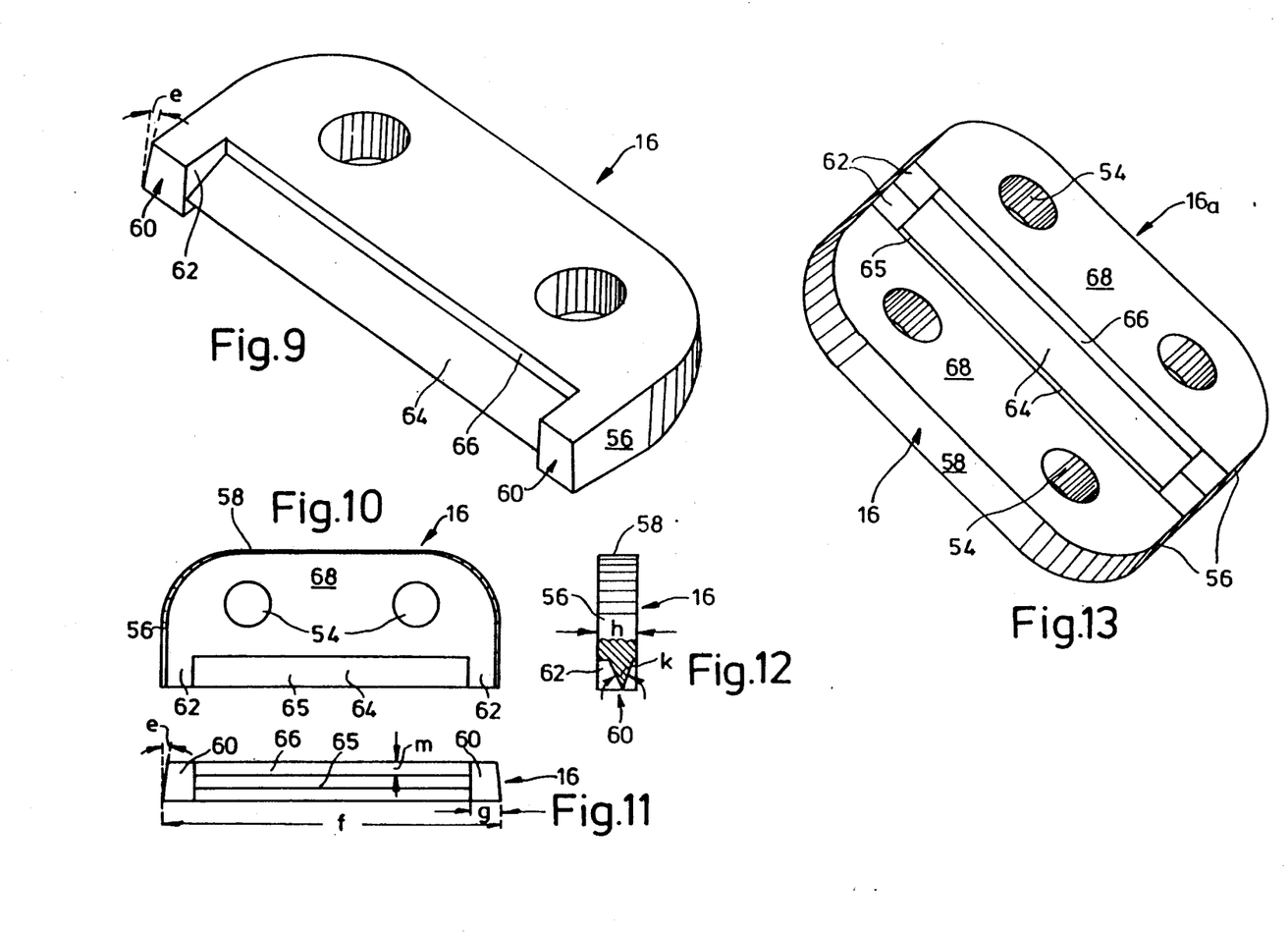
FIG. 9 is a perspective view of the instrument of FIGS. 7 and 8, showing a cutting jaw on an enlarged scale.
FIG. 10 is a plan view on a reduced scale of the cutting jaw shown in FIG. 9.
FIG. 11 is a front view of the FIG. 9 jaw on a reduced scale.
FIG. 12 is a side view of the FIG. 9 cutting jaw.
FIG. 13 is a perspective view of the two cutting jaws shown in FIGS. 7 and 8.

FIG. 7 shows two cutting jaws 16 and 16$_a$ in pressing jaws 21 and 21$_a$. The two cutting jaws 16 and 16$_a$ which are of a length f of about 22 mm and of a height h of about 2.2 mm are fixed in suitably shaped recesses 52 in their respective pressing jaws 21, 21$_a$, more particularly by means of screws (not shown) which pass through bores 54 in the cutting jaws 16, 16$_a$ and which are fixed in a contact bottom portion 53 of the recess 52. Side walls 56, which are inclined at an acute angle e, of the substantially rectangular cutting jaw 16 blend in a rounded configuration into the back 58 of the jaw, the surface of the back in turn being slightly inclined. The side walls 56 each terminate at a respective run-on or check surface 60, the width g of which approximately corresponds to its height h.

A cutting member 64 extends within two horn portions 62 of the cutting jaw 16, 16$_a$, the horn portions 62 providing the run-on or check surfaces 60 and projecting in a battlement-like configuration. The cutting member 64 is fitted to the body of the cutting jaw, forming a wall portion 66, at a spacing m relative to the surface 68 of the jaw, and extends downwardly to the cutting edge 65 which connects the surfaces 60. It will be clear that the run-on or check surfaces 60 permit a substantial reduction in the wedge angle k of the cutting members 64, without the risk of the cutting jaws 16 and 16$_a$ entering into shearing overlapping relationship.

Figure 14:
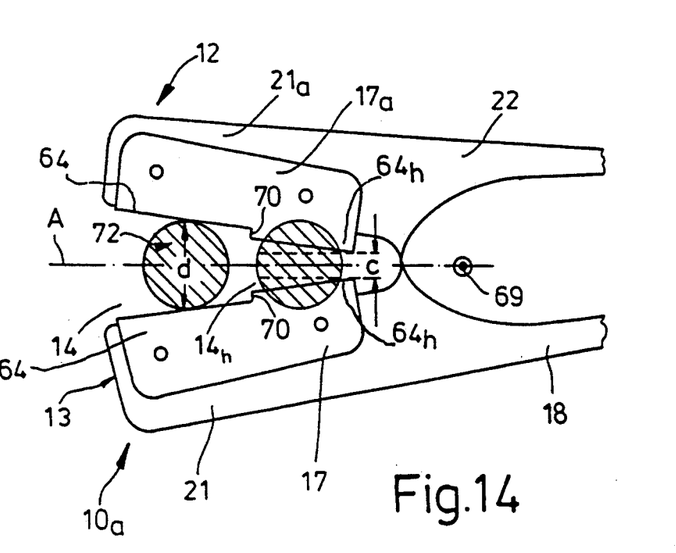
FIG. 14 is a plan view of another head of a nipper instrument with two cutting jaws indicated therein, with the cutting mouth open.
Figures 15, 16:
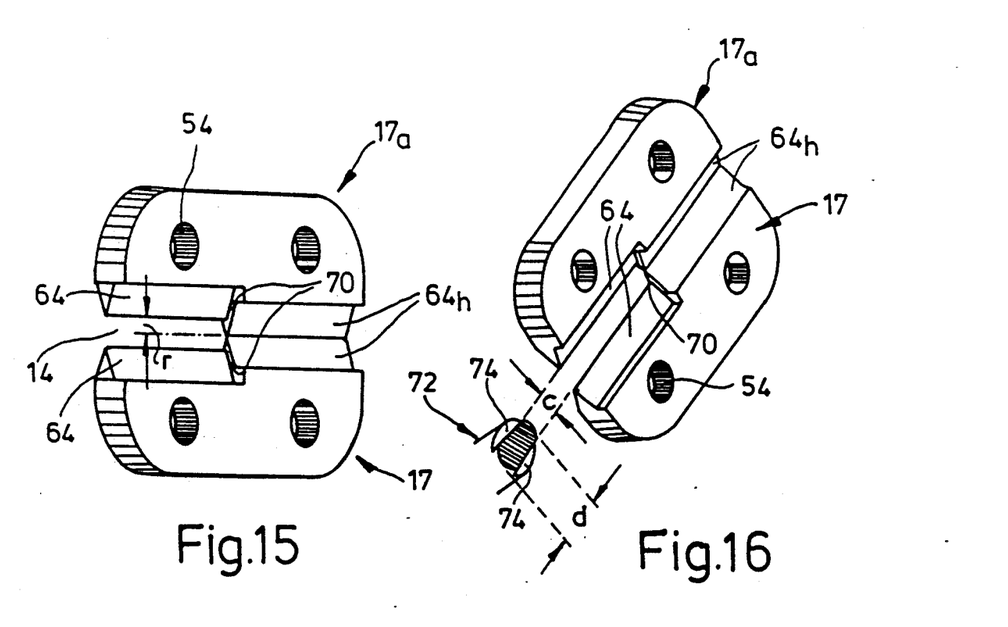
FIGS. 15 and 16 show different perspective views of the two cutting jaws of FIG. 14 with the cutting mouth in the closed condition.

FIG. 14 shows a surgical nipper instrument 10$_a$ in which the pressing jaws 21, 21$_a$ and therewith their cutting jaws 17, 17$_a$ can be pivoted relative to each other about a structural pivot point 69.

The cutting jaws 17, 17$_a$ are stepped a number of times, forming step surfaces 70 which extend transversely with respect to the longitudinal axis A of the nipper instrument. In the illustrated embodiment the cutting jaws are stepped once, that is to say in this case there are two cutting mouth portions 14, 14$_h$ between the cutting members 64 and 64$_h$. The cutting mouth portion which extends from the end 13 of the nipper instrument serves for initially cutting a wire of a diameter d, as indicated at 72, producing a pair of notches 74 at a spacing c which decreases slightly towards the pivot connection; the wire 72 is then moved to the next step or stage 14$_h$ in the cutting mouth in order to be severed between the cutting members 64$_h$ thereof, which are closer together.

The above-described stepped cutting jaw configuration makes it possible to sever larger diameters of for example 5 mm in two severing stages; in that situation, in each of the severing stages, the pair of cutting members 64 and 64$_h$ respectively are operative for only a part of the severing distance as indicated at d, the dimension of said part of the severing distance being determined by the spacing r of the adjacent cutting members 64 and 64$_h$, which in FIG. 14 approximately corresponds to half the dimension d.

Not shown is a configuration in which the cutting edges of the front cutting mouth portion 14 extend inclinedly somewhat relative to the longitudinal axis A of the nipper, as the longitudinal axis of the cutting mouth, in such a way that at the free end of the portion 14 they are slightly closer together than in the interior of the cutting mouth; that arrangement provides that the bottoms or deepest locations of the notches 74 which are produced thereby are parallel to each other.

I claim:

1. A nipper instrument comprising two cutting means at one end thereof defining a cutting mouth, pivotably interconnected nipper arms having two handle ends at the other end of said nipper instrument, one of said cutting means being provided on a pivotable jaw, said pivotable jaw being pivotably connected to one of said nipper arms carrying the other cutting means, the other nipper arm having a cam portion for bearing against a free end of said pivotable jaw wherein the free end of the pivotable jaw is provided with shaft means for carrying a roller which bears against the cam portion characterised in that an abutment surface is provided at the end of the cam portion as a travel limiting means for said pivotable jaw.

2. A nipper instrument according to claim 1 characterised in that the cam portion is part of a guide portion of the other nipper arm and the path of movement of the guide portion is disposed at a spacing relative to the connection between the nipper arms.

3. A nipper instrument according to claim 2 characterised in that the guide portion is part of a head portion of the second nipper arm, which head portion is triangular in side view, wherein one side of the triangle, which extends the handle end of the nipper arm has the cam portion and the other two sides of the triangle start from the end of the cam portion and from the handle end respectively and meet at the connection between the nipper arms.

4. A nipper instrument according to claim 1 characterised in that a straight line connecting the connection between the pivotal jaw and the nipper arm to an axis of said roller includes an angle which is a little larger than 90°, with a straight line which passes through said roller axis and the connection between the nipper arms.

5. The nipper instrument according to claim 4 wherein said angle is between 96° and 104°.

6. A nipper instrument according to claim 1 wherein the distance between a location where said one nipper arm and said pivotable jaw are connected together and said other end of said nipper instrument is shorter than the distance between said location and said roller.

7. A nipper instrument comprising two cutting means at one end thereof defining a cutting mouth, pivotably interconnected nipper arms having two handle ends at the other end of said nipper instrument, one of said cutting means being provided on a pivotable jaw, said pivotable jaw being pivotably connected to one of said nipper arms carrying the other cutting means, the other nipper arm having a cam portion for bearing against a free end of said pivotable jaw wherein an abutment surface is provided on the end of the cam portion as a travel limiting means for the pivotable jaw.

8. A nipper instrument according to claim 7 characterised in that the abutment surface is formed by an abutment projection which extends approximately on a line perpendicular to a guide portion through the connection between the nipper arms.

9. A nipper instrument having a head end, a cutting mouth having a free end which is defined by opposed cutting members on cutting jaws at the head end of the nipper instrument, characterised in that the cutting mouth has at least two zones with a different cutting spacing, wherein each of the cutting members is divided by a step surface extending transversely to a longitudinal axis of the nipper instrument into the cutting members wherein the step surfaces of each cutting member is remote from the free end of the cutting mouth and bear, in the closed condition of the nipper instrument, against the opposed disposed cutting member and wherein a space is defined between the step surfaces of the cutting members proximate to the free end of the cutting mouth characterised in that each cutting jaw has at least one run-on surface which, when the cutting mouth is in a closed condition, bears against a run-on surface on the other cutting jaw.

10. A nipper instrument according to claim 9 characterised in that the longitudinal axis of the nipper instrument forms a line of symmetry for the cutting members.

11. A nipper instrument according to claim 9 characterised in that the axial lengths of the cutting members are approximately equal.

12. A nipper instrument having a head end, a cutting mouth having a longitudinal axis which is defined by cutting members on cutting jaws at the head end of the nipper instrument, characterised in that each cutting jaw has at least one run-on surface which, when the cutting mouth is in a closed condition, bears against a run-on surface of the other cutting jaw wherein the run-on surface of each cutting jaw aligns with a cutting edge thereof, and therein said cutting edge extends between two run-on surfaces on each cutting jaw, and said run-on surfaces of each cutting jaw are provided on two horn portions which are connected by each of said cutting members.

13. A nipper instrument according to claim 12 characterised in that each cutting edge of at least one of the cutting jaws extend somewhat inclinedly relative to the longitudinal axis of the cutting mouth and toward said cutting mouth.

* * * * *